(12) United States Patent
Babaev (10) Patent No.: US 8,048,095 B2
(45) Date of Patent: Nov. 1, 2011

(54) ULTRASOUND LIQUID BLADE SCALPEL DEVICE

(75) Inventor: Eilaz Babaev, Minnetonka, MN (US)

(73) Assignee: Bacoustics, LLC, Minnetonka, MN (US)

( * ) Notice: Subject to any disclaimer, the term of this patent is extended or adjusted under 35 U.S.C. 154(b) by 471 days.

(21) Appl. No.: 12/135,704

(22) Filed: Jun. 9, 2008

(65) Prior Publication Data

US 2009/0306693 A1   Dec. 10, 2009

(51) Int. Cl.
*A61B 17/32* (2006.01)
(52) U.S. Cl. .................................................. 606/167
(58) Field of Classification Search .......... 606/107, 606/166, 169–171, 177, 178, 167; 600/437; 601/1, 2; 83/21, 22, 177
See application file for complete search history.

(56) References Cited

U.S. PATENT DOCUMENTS

| | | | | |
|---|---|---|---|---|
| 5,322,504 A * | 6/1994 | Doherty et al. | ............... | 606/167 |
| 6,458,143 B1 * | 10/2002 | Sugai | ............... | 606/169 |
| 6,663,554 B2 * | 12/2003 | Babaev | ............... | 600/2 |
| 6,799,729 B1 * | 10/2004 | Voic | ............... | 239/102.2 |
| 2003/0236560 A1 * | 12/2003 | Babaev | ............... | 607/50 |
| 2006/0178579 A1 * | 8/2006 | Haynes | ............... | 600/437 |

* cited by examiner

*Primary Examiner* — S. Thomas Hughes
*Assistant Examiner* — Katherine M Shi (57) ABSTRACT

An ultrasound assisted liquid blade cutting device such as a scalpel that may be used for routine surgical operations is disclosed in this invention. The ultrasound scalpel comprises an ultrasound generator, ultrasound transducer, transducer tip, a cavity on the transducer tip using a liquid spray shaped to form a cutting surface. The spray serves as a carrier medium for the applied ultrasound energy which enhances the features and performance of the scalpel. Ultrasonic energy transmitted from the transducer tip assists the transport of the liquid to a liquid blade formed outside of the cavity. The ultrasound energy focuses and activates the liquid to allow cutting of tissue with the liquid blade. This device may be utilized for cutting through skin and/other soft tissues during surgical operations, thereby enhancing cutting efficacy, decreasing and/or eliminating necrosis formation.

21 Claims, 5 Drawing Sheets

ULTRASOUND LIQUID BLADE SCALPEL DEVICE

BACKGROUND OF THE INVENTION

This present invention relates generally to a surgical instrument that can use ultrasound to influence and energize a liquid such as water to form the blade of a knife or scalpel with improved cutting abilities. More particularly the invention relates to an ultrasound liquid scalpel having improved properties for use during surgical operations involving cutting through skin tissues, organ tissues and other tissues.

Generally, a scalpel is a tool for cutting through skin and/or other soft tissues during surgeries. U.S. Pat. No. 2,650,426 to Montelius, U.S. Pat. No. 5,055,106 to Lundgren and U.S. Pat. No. 5,078,724 to Takase describe examples of scalpels known in the prior art. These surgical scalpels comprise basically a cutting edge, such as a blade attached to a handle. In addition to use in surgery scalpels generally, as well as the present invention in particular, may be used in a variety of cutting application in the arts, crafts and other precision cutting processes for cutting wood, paper, plastics, foams and other natural and man-made materials. The size and shape of the blade and handle vary depending on the particular application of use.

Due to problems associated with such surgical scalpels such as, but not limited to, the application of too much pressure on the cutting area, trauma, and scaring, ultrasonic scalpels using metal blades were developed. Ultrasonic scalpels are well known in the art and used widely for surgical operations. An ultrasonic scalpel can reduce bleeding and reduce the amount of pressure needed during cutting. As such, ultrasonic scalpels using metal blades may eliminate some of the trauma associated with pressure applied to the cut and with the surgery in general.

Using metal bladed ultrasonic scalpels can reduce the scarring and bleeding associated with surgical operations compared to ordinary scalpels lacking ultrasound energy. Examples of related devices are disclosed in U.S. Pat. No. 5,167,725 to Clark et al, and U.S. Pat. No. 6,514,267 to Jewett. The cauterization effect of ultrasound is also utilized in related devices such as U.S. Pat. No. 5,263,957 to Davison and U.S. Pat. No. 5,324,299 to Davison et al.

Despite their advantages, the prior art ultrasonic scalpels fail to effectively cut through skin and/or soft tissue without inflecting collateral damage on the skin and/or soft tissue being cut. The infliction of collateral damage occurs because most prior art ultrasonic scalpels are designed to be used with longitudinal motions which either result in excessive bleeding from the incision, require the application of excessive pressure on tissue, or are insufficient for cutting without damaging the surrounding skin and/or soft tissue. Such trauma to viable tissue can impede the healing potential. Necrosis (i.e., death of cells and living tissue) may also result from the trauma. Necrosis is caused by the continuous friction created from the blade's cutting edge and/or surface being in continuous contact with the skin and/or tissue as it is chit, leading to acoustic burns. Such continuous contact is the outcome of the blade's repeated longitudinal motion during cutting. The resulting damage to the surrounding skin and/or tissue is often irreversible.

Cutting devices using water as a blade material such as; U.S. Pat. No. 5,944,686 to Patterson et al., U.S. Pat. No. 6,511,493 to Moutafis et al and U.S. Pat. No. 7,122,017 to Moutafis et al provide a very highly pressurized stream of water that may be used for cutting tissue. As a result of the high discharge pressures, relatively large volumes of water are discharged from the cutting devices. To facilitate collecting this water, the devices generally have a return orifice opposite the supply orifice within a cavity, thereby confining the water cutting surface entirely within the cavity. Although this configuration is effective at returning the water for collection, it effectively shrouds the cutting blade making it very difficult to access on the body to be cut. Accessing body tissue often requires pressing the device into the surrounding tissue so that the water cutting surface may make contact with the tissue being cut. This pressure may be necessary to access the tissue, but may also result in extensive pain to the patient during the procedure, especially when cutting tissue in injured or sensitive areas of the patients body.

Cutting devices using water and ultrasound for debridement have been developed. Examples within the prior art include, U.S. Pat. No. 7,025,737 to Soring et al., U.S. Pat. No. 6,569,099 to Babaev and U.S. App. No. 20070287934 to Babaev. These devices may be used for debridement but do not disclose a scalpel using a liquid influenced by ultrasound energy to form a knife blade that is useable for routine surgical applications.

SUMMARY OF THE INVENTION

An ultrasound assisted liquid blade cutting device and associated methods of use enabling relatively pain-free incision is provided. As described herein, the invention is used for procedures in somewhat the same manner other scalpels and cutting devices are used. Example uses include surgical cutting on skin, organs and other tissues of a patient. Non-surgical uses of the invention are also possible. The invention may be useful for cutting wood, plastics, foam or other materials for purposes of art, crafts, hobbies and manufacturing applications were precise hand manipulated cutting is required.

The device comprises an ultrasound generator driving an ultrasound transducer connected to an ultrasound transducer tip containing a cavity. The transducer tip preferably contains a supply tube to transport a liquid to the cavity. The cavity is a hollowed out area within the transducer tip, preferably of a parabolic shape defined by walls within the transducer tip. When driven or otherwise activated by the ultrasound generator, the ultrasound transducer induces ultrasonic vibrations within the tip, causing ultrasonic waves carrying ultrasonic energy to be released from the various surfaces of the tip, including the walls defining the cavity. Within the cavity, the liquid may be transformed into a spray by ultrasound waves emanating from the walls defining the cavity. In the alternative or in combination, the ultrasound waves may push the liquid stream within the cavity towards the focal point of the cavity. The cavity generally has a focal point towards which the ultrasound waves and liquid are directed. The ultrasound waves and liquid directed towards the focal point creates a cutting focus forming a liquid blade, preferably outside of the opening of the cavity. The cutting focus may overlap or diverge from the focal point of the cavity.

Configuring the walls of the cavity as to form a parabola in at least two dimensions may focus the ultrasonic energy emanating from the walls of the cavity towards the focal point of the parabola. In a preferred embodiment, the focal point of the parabola lies outside the cavity, so that the ultrasonic energy emitted from the cavity may be concentrated towards a point outside of the perimeter of the cavity.

When the transducer tip is ultrasonically vibrated, cavitations may form within the liquid. Cavitations formed in the liquid may have benefits such as, but not limited to, further nebulizing the liquid, producing ozone, deactivating microorganisms, reducing patient pain levels and improving debridement.

Known ultrasonic cutting devices have orthogonal dimensions to the lateral axis at their distal end and proximal end. Generally the distal end orthogonal dimension is greater than the proximal end orthogonal dimension, making use of the device cumbersome. An advantage of the present invention, is that the transducer tip's distal end orthogonal dimension does not need to be greater than the transducer tip's proximal end orthogonal dimension making use of the invention much more convenient, particularly where maneuverability is an issue such as for internal cuttings.

One of the major advantages of the present invention is improved and more effective cutting of skin and/or soft tissue. The use of ultrasonic energy to form a liquid blade, and then use the liquid blade in cooperation with the ultrasonic energy produces a number of substantial benefits over the prior art.

Another aspect of the device of the present invention may be to provide an ultrasonic liquid blade cutting device that does not require the use of metal blades.

Another aspect of the device of the present invention may be to provide an ultrasonic liquid blade cutting device that may effectively cut through skin and/or soft tissue easier and/or inflicting less trauma than conventional scalpels.

Another aspect of the device of the present invention may be to provide an ultrasonic liquid blade cutting device that will minimize blood loss through cauterization, protein denaturization, coagulation and/or sealing both interoperatively and postoperatively.

Another aspect of the device of the present invention may be to provide an ultrasonic liquid blade cutting device that will allow tissue differentially dissected during its use.

Another aspect of the device of the present invention may be to provide an ultrasonic liquid blade cutting device that may be used without generating sharps for disposal.

Another aspect of the device of the present invention may be to prevent, reduce and/or eliminate necrosis of tissues.

These and other aspects of the invention will become more apparent from the written description and figures below.

BRIEF DESCRIPTION OF THE DRAWINGS

The present invention will be shown and described with reference to the drawings of preferred embodiments and will be clearly understood in details. Like elements of the various embodiments within the figures are equivalently numbered.

DETAILED DESCRIPTION OF THE INVENTION

Figure 1:
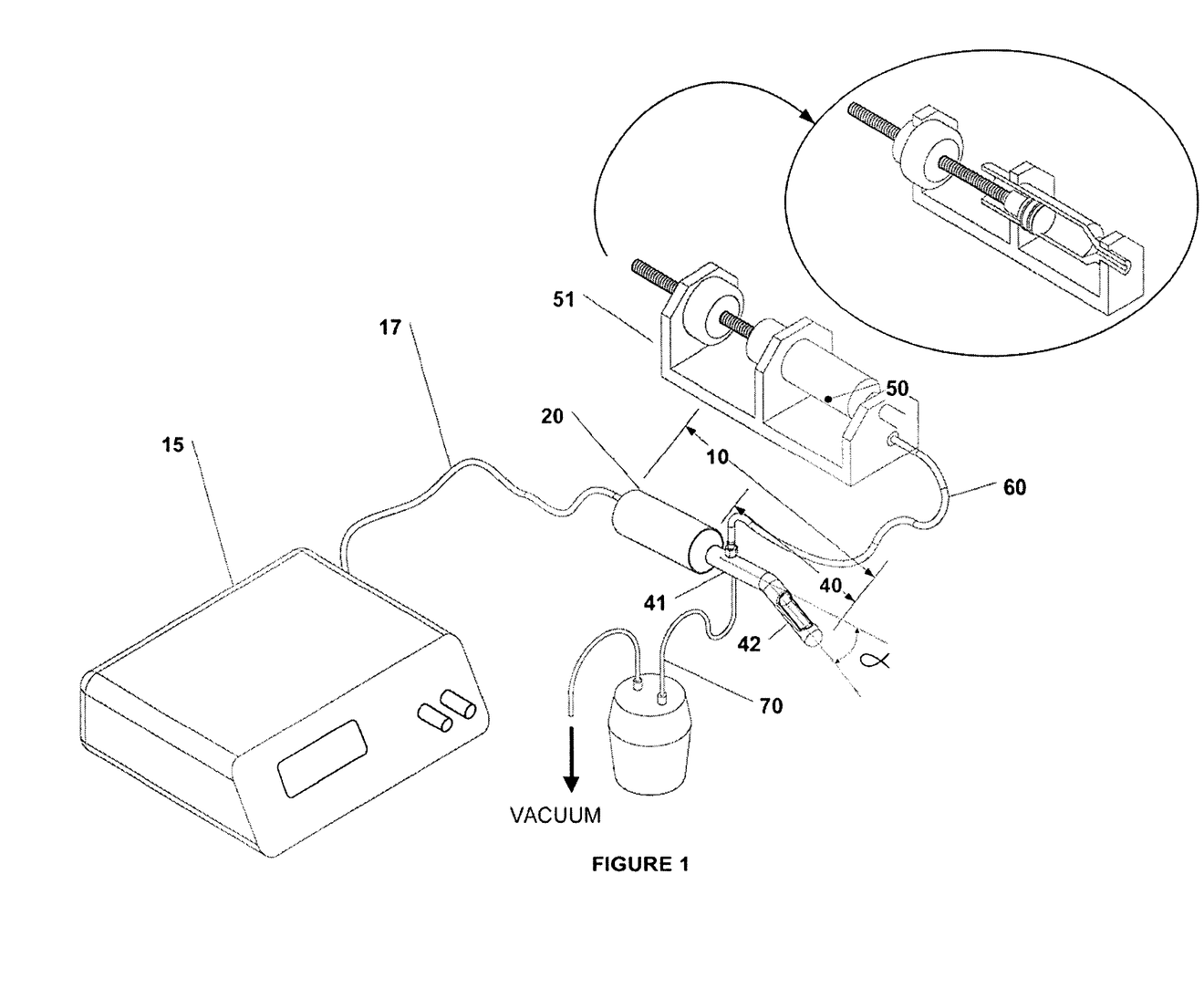
FIG. 1 depicts the ultrasonic liquid blade cutting device of the present invention.

The present invention is an ultrasonic liquid blade cutting device that may be used for various surgical operations including cutting through skin tissue, organ tissue and/or other soft tissues. FIG. 1 depicts one possible embodiment of the ultrasonic liquid blade cutting device of the present invention. The depicted embodiment of the present invention comprises an ultrasound generator 15 with an electrical cord supplying the ultrasound generator 15 power, such as standard AC or battery power from a power source. The ultrasound generator 15 is in electrical communication with an ultrasound transducer 20 through a signal connector 17. A hand piece 10 contains the ultrasound transducer 20 driven by the ultrasound generator 15, a housing surrounding the ultrasound transducer 20 that provides a gripping surface and an transducer tip 40 or horn connected to the distal end of the ultrasound transducer 20.

The transducer tip 40 may be connected to transducer 20 either directly or through a mechanical interface such as by threading, welding and/or other means readily recognizable by people of ordinary skill in the art. The transducer tip 40, or portions of the transducer tip 40 may be removable from the hand piece 10 for cleaning, sterilization and/or replacement as would be understood by those skilled in the art upon review of this disclosure. The transducer tip 40 may be fabricated from metals such as, but not limited to, alloys of titanium, aluminum and/or steel.

Ultrasound generators and ultrasound transducers are well known in the art and will not be described in detail herein. However, the ultrasound generator 15 should be capable of producing an electrical signal of a sufficient alternating voltage to drive the ultrasound transducer 20. The ultrasound transducer 20 converts the alternating voltage into mechanical motion as to induce the transducer tip 40 to vibrate. Preferably transducer tip 40 is induced to vibrate approximately in resonance. The amplitude of the vibrations produced may be any in the ultrasound spectrum, but are typically between approximately 1 micron and approximately 300 microns. The preferred amplitude range is approximately 60 microns-100 microns. The recommended amplitude value is approximately 80 microns.

The electrical signal produced by ultrasound generator 15 should also be sufficient to drive the ultrasound transducer 20 to induce transducer tip 40 to vibrate approximately in resonance at any frequency within the ultrasound spectrum, such as, but not limited to, between approximately 15 kHz and approximately 3 MHz. The preferred frequency range for the transducer tip 40 is 15 kHz to 50 kHz with a recommenced frequency of approximately 30 kHz.

Ultrasound transducer 20 may be driven with a continuous wave or pulsed frequency signal supplied by ultrasound generator 15. Driving transducer 20 with a continuous wave tends to induce the release of standing waves from tile various surfaces of tip 20, while a pulsed frequency reduces or avoids the release of standing waves. The pulsed frequency signal generates less heat and may increase the longitudinal force of the induced vibrations as a result of the on/off cycle changes. The electrical signal may be changed depending on the desired features of the released ultrasound waves for the particular application. For example, inducing the release of standing waves may be helpful to produce or increase cavitation effects.

The wave form of the electrical signal may be sinusoidal, rectangular, trapezoidal and/or triangular. In addition, the electrical signal from the ultrasound generator 15 may be fixed or modulated. Ultrasound generator 15 may include feedback control to adjust the signal.

A housing serving as a handle for the ultrasonic liquid blade cutting device may isolate the ultrasound transducer 20 from the device operator. Surgeons and/or users of the ultrasonic liquid blade cutting device could hold the housing during surgical operations to manipulate the device. The housing provides a surface appropriate for hand manipulation by the surgeon and/or user while allowing the user to avoid direct contact with vibrations within the device. The housing may extend over the entire ultrasound transducer 20 and/or may partially enclose portions of the transducer tip 40.

The transducer tip 40 receives a liquid 50, typically through a supply tube 60. Supply tube 60 may enter the transducer tip 40 longitudinally through the ultrasound transducer 20 and/or handle. The liquid 50 may also be delivered radially through means external to the device. Various liquids such as, but not limited to, tap water, distilled water, saline, and/or other therapeutic agents such as, but not limited to, anti-inflammatories and/or antibiotics may be used with the device. The liquid 50 is preferably provided by a pump 51 to the supply tube 60. Various pumps may be utilized to provide liquid 50 to supply tube 60. For example, pump 51 may be a syringe pump or other positive displacement pump. Depending on the desired operating characteristics and use of the device, liquid 50 may be provided at a relatively low pressure of approximately 1 to 100 psi, or at higher pressures of tip to approximately 20,000 psi using available prior art devices. The pump and supply tube provided must be compatible with the pressure ranges actually used. If the transducer tip 40 requires additional cooling beyond that provided by the flow and/or atomization of liquid 50, transducer tip 40 may be equipped with additional cooling capabilities. A possible means of equipping tip 40 with cooling capabilities is to provide internal lumen within tip 40 for circulating, a cryogenic fluid such as but not limited to liquid nitrogen. Other means of equipping tip 40 with cooling capabilities, readily recognizable by those of ordinary skill in the art, are equally possible.

The transducer tip 40 may also include a return tube 70 in some embodiments. The return tube 70 may remove liquid 50, tissue and other materials and fluids in the incision site and/or the cavity 100. The return tube 70 preferably connects between the transducer tip distal end 42 and a vacuum source. Although the use of a vacuum source is preferred, with proper alignment of the orifice 80 and return orifice 90 the kinetic energy of the liquid can be used to collect some of the excess fluid in the return tube 70 and then through the tube for removal.

An aspirator may be used to remove fluids and other materials from the surgical area. The aspirator may be integrated with the transducer tip 40. Alternatively or in combination, the aspirator may be a device independent and separate from the transducer tip 40.

Figure 2:
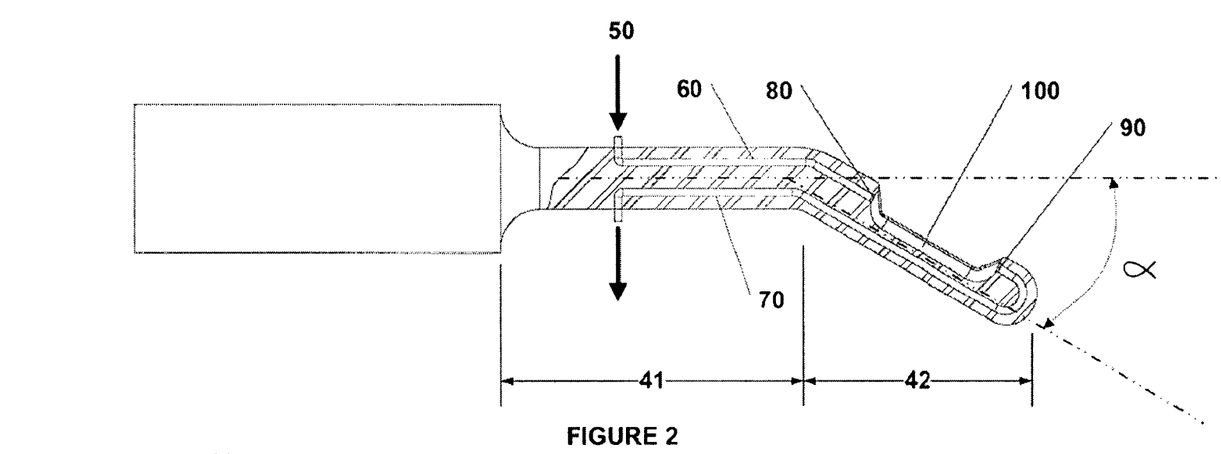
FIG. 2 depicts a cross-sectional view of a portion of the transducer tip of the present invention.

FIG. 2 depicts a partial view of the transducer tip 40. The longitudinal axis of the transducer tip distal end 42 may be positioned to create an angle α with the longitudinal axis of the transducer tip proximal end 41. In the preferred embodiment α may vary from approximately 0 to 45 degrees.

The transducer tip distal end 42 includes a cavity 100 that receives the liquid 50 from an orifice 80 via the supply tube 60. The orifice 80 may be of any geometric shape, but is typically circular, oval or slot shaped. A circular shape is preferred for the orifice 80. The return tube 70 originates at a return orifice 90 on the transducer tip distal end 42. The cavity is generally of an open parabolic shape preferably elongated along the transducer tip's longitudinal axis. The cavity may be defined by at least one wall with an open perimeter edge. Preferably the cavity is defined by a distal end wall, a proximal end wall and two side walls all terminating at an open perimeter edge.

Even though the transducer tip distal end 42 includes cavity 100, as FIG. 2 shows, at its largest dimension, the transducer tip's distal end 42 orthogonal dimension does not need to be greater than the transducer tip's proximal end largest orthogonal dimension. This allows the device to provide improved maneuverability and convenience, particularly where tight space may be an issue such as for internal cutting in hard to reach locations.

Figure 3:
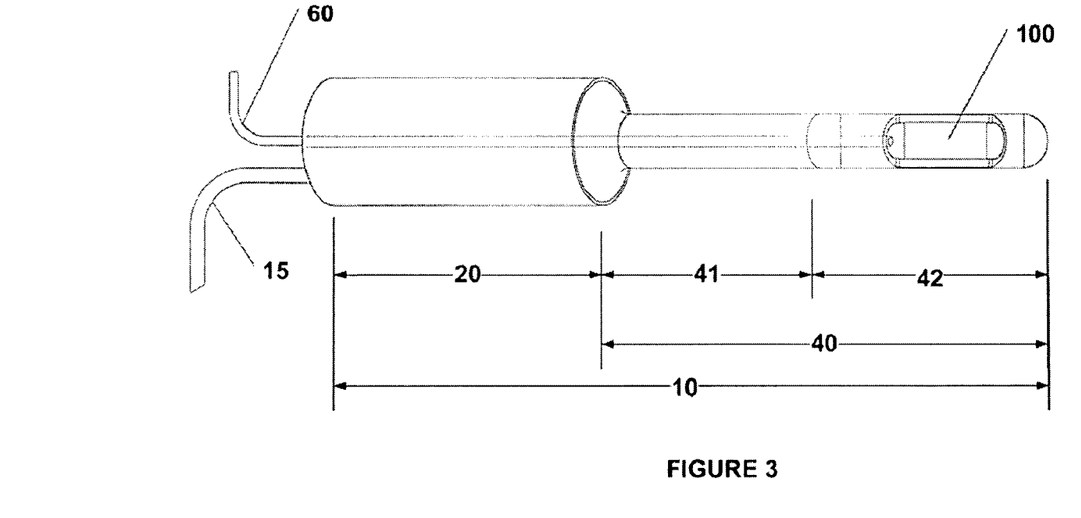
FIG. 3 depicts a planar view of hand piece portion of the ultrasonic scalpel.

FIG. 3 depicts a plan view of the hand piece portion of the ultrasound liquid cutting device. The supply tube 60 may enter tile hand piece and run alone tile longitudinal axis through the ultrasound transducer 20 and the transducer tip 40 to reach the transducer tip proximal end 41.

Figure 4:
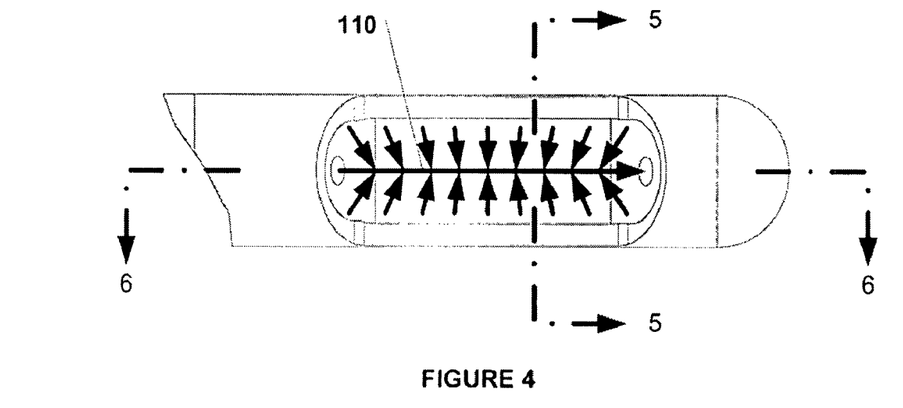
FIG. 4 depicts a planar view of the transducer tip.

Liquid 50 may flow along the surface of the cavity wall. Alternatively, liquid 50 may leave the orifice 80 and travel through the interior of the cavity 100 as a stream without contacting the cavity wall. Furthermore, the liquid 50 may be reflected off the cavity wall and dispersed within the cavity 100. It is possible that liquid 50 may be directed to the return orifice 90 so that at least a portion is removed from the cavity 100. In any of the above alternatives, as shown in FIG. 4 the liquid 50 is being directed towards the focal point(s) of the cavity 100. In addition to directing liquid 50 towards the focal point of cavity 100, liquid 50 may be transformed into a spray by the ultrasound energy being emitted from the interior of the cavity 100. The ultrasound shaves released from the interior of the cavity 100 tend to push the spray in the direction the ultrasound waves are traveling. This direction is generally orthogonal to the surface of the cavity wall which is primarily transverse to the longitudinal axis of the transducer tip distal end 42. As such, the spray is directed by the ultrasound waves to the focal point of cavity 100. Directing liquid 50 towards the focal points of cavity 100 forms a series of cutting foci connecting to form a liquid blade 110. Liquid blade 110 is preferably along a line, parallel to the longitudinal axis of the transducer tip distal end 42 but located outside the outer edge of the cavity 100. The location of the liquid blade 110 is primarily defined by the parabolic shape of the cavity 100 directing the ultrasound waves, the characteristics of the ultrasound waves and the characteristics of the fluid stream.

Figure 5:
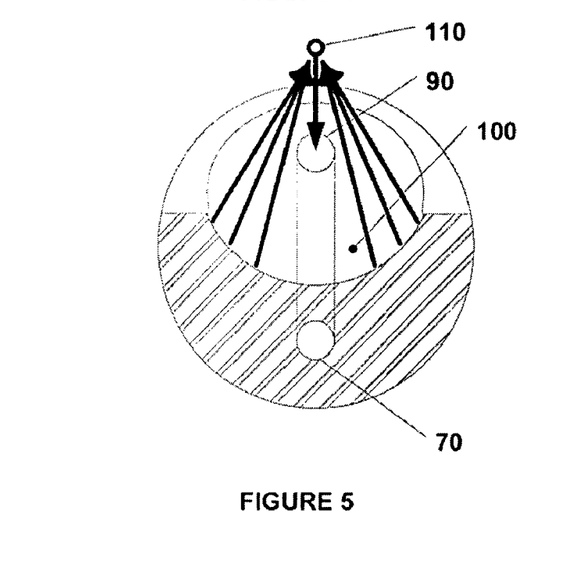
FIG. 5 depicts a cross-sectional end view of one possible embodiment of the transducer tip.

In FIG. 5 a cross sectional end view of the transducer tip distal end 42 is depicted. In this embodiment, the return tube 70 extends to a return orifice 90 located near the edge of the distal wall of the cavity 100. The ultrasonic energy and the spray formed from the liquid 50 are directed to the focal line of the cavity 100, forming liquid blade 110. The location of the liquid blade 110 is determined by the shape of the cavity 100, the characteristics of the ultrasound energy and the physical, chemical and energy characteristics of the fluid stream.

The use of liquid 50 and ultrasound energy to form the ultrasonic liquid blade used with this cutting device has the substantial benefit that surgical cutting operations may be performed without generating sharps for disposal. In addition to the avoided expense of obtaining, handling and disposing of sharps, their lack of presence substantially reduces the safety risks associated with surgical cutting operations, particularly with regards to the transmission of blood born pathogens.

Figure 6:
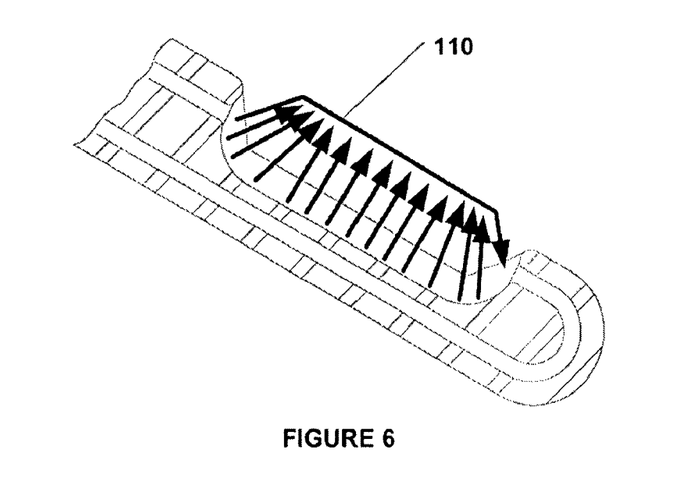
FIG. 6 depicts a cross-sectional side view of an alternative embodiment of the transducer tip.
Figure 7:
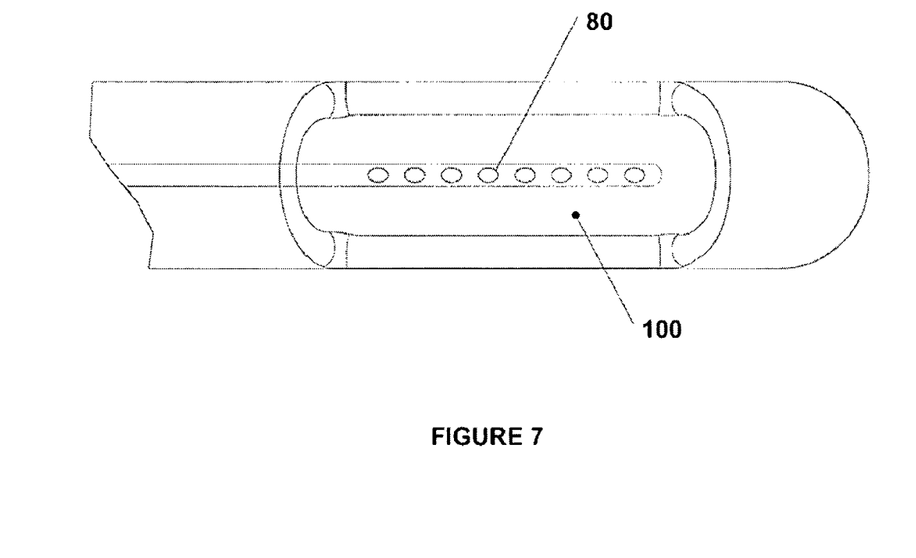
FIG. 7 depicts a planar view of an alternative embodiment of the transducer tip.
Figure 8:
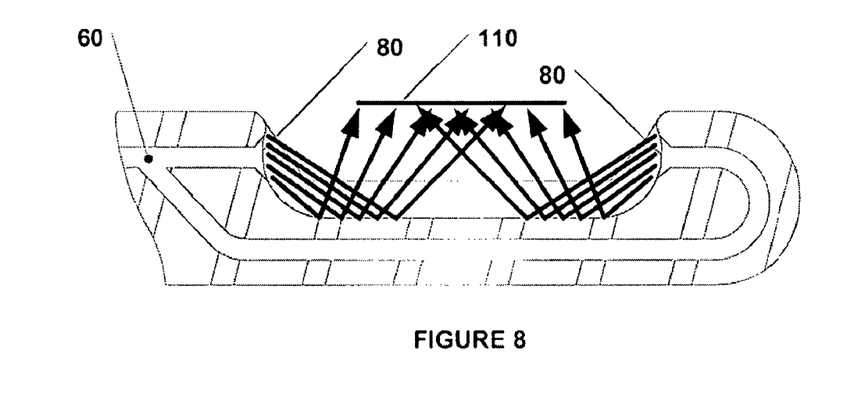
FIG. 8 depicts a cross-sectional view of an alternative embodiment of the transducer tip.
Figure 9:
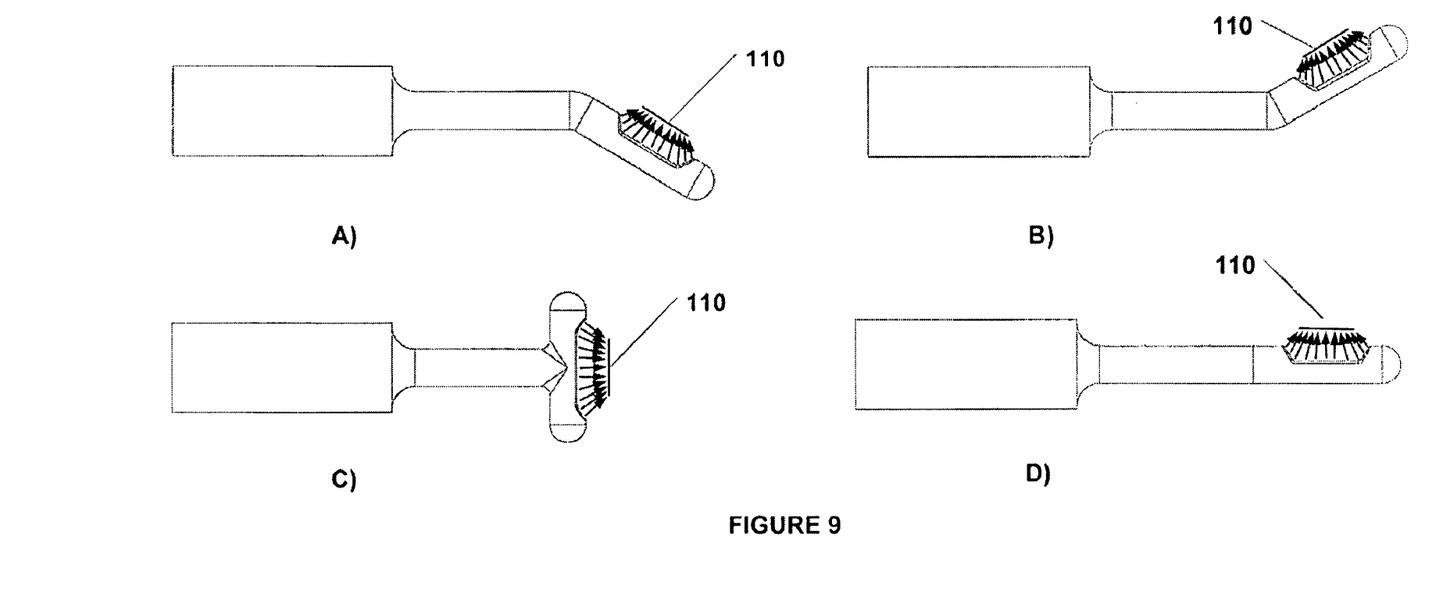
FIGS. 9A-D depicts alternative embodiments of the transducer tip portion of the hand piece.

In FIG. 6 a cross sectional view along the longitudinal axis of the transducer tip distal end 42 is shown depicting the liquid blade 110 in its preferable location above the perimeter of cavity 100. Delivery of the ultrasound energy to the focal line of cavity 100 overlapping the liquid blade 110 is enhanced by the presence of the liquid 50 in the form of a spray, since the liquid 50 serves as a fluid coupling medium, greatly enhancing the transmission of ultrasound energy released from the walls of cavity 100.

Ultrasound transmission through air is relatively inefficient. Utilizing the liquid 50 forming the ultrasonic liquid blade 100 as a fluid coupling medium greatly improves the transmission of the ultrasound energy released from the cavity 100. In addition, the liquid blade 110 serves as a structure allowing the ultrasound energy to form cavitations as the ultrasound energy is delivered from the cavity 100 to the liquid blade 110. When the tip is ultrasonically vibrated, cavitations may form within the liquid 50. In addition, liquid 50 within cavity 100 may be atomized into a spray. If a piezoelectric transducer is used to induce the transducer tip 40 to vibrate approximately in resonance, then the voltage of the electrical signal driving the transducer will largely control the degree to which liquid 50 is cavitated and/or atomized. At low voltages, liquid 50 within and/or outside the cavity 100 will be cavitated to a small degree. As the voltage increases, the amount of cavitations within liquid 50 is increased. Further increasing die voltage will eventually induce atomization of liquid 50. Regardless of whether liquid 50 is atomized and/or cavitated, the presence of liquid within and/or beyond the confines of the cavity 100 may couple the transmission of ultrasonic energy released from the walls of the cavity 100 to the wound and/or tissue to be cut.

The cavitation of liquid 50, as well as the mechanical energy associated with the focused ultrasound energy can be used to assist the production of ozone from the oxygen associated with the air and/or liquid. The ozone produced may be utilized to assist the ultrasound energy to disrupt cellular materials and inactive pathogens. Thereby, the ozone may provide therapeutic disinfecting properties to help the patient resist operative and post-operative infections.

In addition to pathogen deactivation, the combination of ultrasound energy and cavitation effects can be utilized to cooperatively minimize blood loss through cauterization, protein denaturization, coagulation and/or sealing both during the surgical procedure and during postoperative healing. The combination of ultrasound energy induced mechanical vibrations and cavitation effects may also be utilized to prevent, reduce and/or eliminate necrosis of tissues.

The ultrasonic energy transmitted via liquid 50 may be used to irrigate the surgical area. Additionally, the transmitted ultrasonic energy may provide for less painful treatment. The ultrasonic energy and/or the waves carrying it may elicit a change in the membrane permeability of deep cellular structures such as, but not limited to, axons and somas, decreasing the sensation of pain in surgical area. Additionally or in combination, the mechanical energy generated by directing ultrasound waves towards a focal point may interact with nerve cells as to provide an analgesic effect.

The parabolic shape of the cavity 100 of the disclosed device will tend to direct ultrasound energy, mechanical energy, and liquid 50 towards the focal point or line of cavity 100. If liquid 50 is introduced through orifice 80 into cavity 100 at high pressures a jet stream spray traveling across cavity 100 and into return orifice 90 may be produced. When transducer tip 40 is induced to vibrate, ultrasound waves released from the wall surfaces of cavity 100 may direct the jet stream towards the focal point and/or focal line of cavity 100. Liquid 50 may be transported through return tube 70 either with the assistance of a vacuum source, or simply using the liquid's kinetic energy and gravity. Inducing the transducer tip 40 to ultrasonically vibrate may result in atomizing or nebulizing of at least a portion of the liquid 50 in the spray. If liquid 50 is introduced to the cavity 100 at low pressures it may be directly atomized or nebulized by the ultrasonic energy emanating from the cavity's wall surfaces, whether or not the fluid actually reaches the wall surfaces. In any result, an atomized spray may be produced which may then be directed toward the focal point(s) of cavity 100.

Adjustment of the characteristics of the ultrasound energy and/or focal point of cavity 100 may allow the user to select operating conditions so that the ultrasonic liquid blade cutting device will allow the operator to differentiate between tissue during use based on tissue properties. For example, the device may be adjusted so that it will cut soft organ tissue, but not other tissues such as nerve tissues, tendons, ligaments or bone tissues. Furthermore, the device may be adjusted so that it will allow cutting with only minimal pressure being exerted by the operator on the tissue being cut, as to minimize pain being generated by instrument pressure. This feature is present with this invention because the mechanical motion of the fluid and ultrasound provided by the device does not depend on mechanical force from the operator alone to create the incision.

In addition to the internal and external liquid delivery methods described previously, as another alternative, depicted in FIG. 7 cavity 100 may have a plurality of orifices 80 arranged in a slot shape. Under this embodiment, the discharge pressure of liquid 50 can be utilized in cooperation with the ultrasound waves released from the wall surface of cavity to direct liquid 50 beyond the outer perimeter of cavity 100 to form the liquid blade 110.

Another liquid 50 delivery method, shown in FIG. 8 depicts an embodiment having a supply tube 60 with a plurality of orifices 80 shown in a slot shape. The orifices are positioned to direct liquid 50 away from the perimeter of the cavity 100 so that the liquid 50 is reflected off the wall of the cavity 100 towards the focal point and/or focal line of the cavity 100. Under this embodiment, the discharge pressure of the liquid 50 is used assist the ultrasound waves in directing liquid 50 beyond the outer perimeter of the cavity 100, as to form the liquid blade 110.

As shown in FIGS. 9A-D, the transducer tip distal end 42 has a longitudinal axis and transducer tip proximal end 41 also has a longitudinal axis. An angle $\alpha$ may be formed at the intersection of the transducer tip distal end 42 longitudinal axis and the transducer tip proximal end 41 longitudinal axis. The liquid blade longitudinal axis is preferably parallel with the longitudinal axis of the transducer tip distal end 42. Various embodiments having varying angles $\alpha$ of the hand piece are possible, which may be preferred for the various uses of the device. FIG. 9A shows a device with an angle $\alpha$ of less than 90-degrees. FIG. 9B shows a device with an angle $\alpha$ of greater than 180-degrees. FIG. 9C shows a device with an angle $\alpha$ equal to 90-degrees. FIG. 9D shows a device with a horizontal alignment with an angle $\alpha$ equal to approximately 0-degrees.

Combinations of the above embodiments and other embodiments will be apparent to those having skill in the art upon review of the present disclosure. The scope of the present invention should be determined with reference to the appended claims, along with the full scope of equivalents to which such claims are entitled.

It should be appreciated that elements described with singular articles such as "a", "an", and/or "the" and/or otherwise described singularly may be used in plurality. It should also be appreciated that elements described in plurality may be used singularly. Although specific embodiments of devices and methods have been illustrated and described herein, it will be appreciated by those of ordinary skill in the art that any arrangement, combination, and/or sequence that is calculated to achieve the same purpose may be substituted for the specific embodiments shown. It is to be understood that the above description is intended to be illustrative and not restrictive.

Combinations of the above embodiments and other embodiments as wells as combinations and sequences of the above methods and other methods of use will be apparent to individuals possessing skill in the art upon review of the present disclosure. The scope of the claimed apparatus and methods should be determined with reference to the appended claims, along with the full scope of equivalents to which such claims are entitled.

I claim:

1. An ultrasound assisted liquid blade cutting device comprising:
   a. an ultrasound generator;
   b. an ultrasound transducer producing ultrasonic energy within a housing;
   c. the ultrasound transducer in electrical communication with the ultrasound generator;
   d. a transducer tip connected to the ultrasound transducer, the transducer tip having a cavity within a region of the distal end of the tip having orthogonal dimensions no larger than the orthogonal dimensions of the proximal end of the tip and receiving a liquid through a supply tube;
   e. the liquid forming a spray within the cavity;
   f. the spray used as a coupling medium for the ultrasound energy;
   g. the cavity generating ultrasound energy; and
   h. the cavity directing the spray and the ultrasound energy to produce a liquid blade, the liquid blade being formed by a series of cutting foci along a line parallel to the longitudinal axis of the transducer tip distal end.

2. The device of claim 1 having the transducer tip constructed of a material selected from the group consisting of stainless steel, titanium allow and aluminum alloy.

3. The device of claim 1 wherein the cavity has substantially a parabolic shape.

4. The device of claim 1 also having an aspirator integral with the transducer tip.

5. The device of claim 1 also having a vacuum source in fluid communication with the transducer tip.

6. The device of claim 1 also having an orifice directing the liquid into the cavity through the supply tube.

7. The device of claim 1 wherein the orifice directing the liquid into the cavity through the supply tube has a slot shape.

8. The device of claim 1 further comprising a parabola formed by the wall or walls of the cavity in at least two dimensions.

9. The device of claim 1 further comprising the liquid blade of the cavity positioned outside the cavity perimeter.

10. The device according to claim 1 characterized by the ultrasound generator being capable of producing an electrical signal to induce the ultrasound transducer and transducer tip to vibrate approximately in resonance with a frequency of the vibrations being approximately between 15 kHz and 3 MHz.

11. The device according to claim 1 characterized by the ultrasound generator being capable of producing an electrical signal to induce the ultrasound transducer and transducer tip to vibrate approximately in resonance with a frequency of the vibrations being approximately 30 kHz.

12. The device according to claim 1 characterized by the ultrasound generator being capable of producing an electrical signal of a voltage sufficient to induce the ultrasound transducer and transducer tip to vibrate approximately in resonance with the amplitude of the vibrations being approximately between 1 micron and 300 microns.

13. The device according to claim 1 characterized by the ultrasound generator being capable of producing an electrical signal of a voltage sufficient to induce the ultrasound transducer and transducer tip to vibrate approximately in resonance with the amplitude of the vibrations being approximately 80 microns.

14. The device according to claim 1 generating a wave form selected from the group consisting of sinusoidal, rectangular, trapezoidal and triangular.

15. The device according to claim 1 wherein the ultrasound energy is selected from the group consisting of continuous wave or pulsed frequency.

16. The device according to claim 1 characterized by the ultrasound generator being capable of producing an electrical signal of a voltage sufficient to induce cavitations within the liquid.

17. The device according to claim 1 characterized by the ultrasound generator being capable of producing an electrical signal of a voltage sufficient to nebulize the liquid.

18. The device according to claim 1 also having a return tube receiving at least a portion of the liquid through a return orifice located in the cavity.

19. The device according to claim 1 wherein the liquid is supplied to the supply tube at a pressure between approximately 1 psi and 20,000 psi.

20. The device according to claim 1 wherein the liquid is supplied to the supply tube at a pressure between approximately 1 psi and 100 psi.

21. The device according to claim 1 wherein the ultrasound tip has a proximal end with a longitudinal axis and a distal end with a longitudinal axis with an angle formed at their intersection.

* * * * *